(12) United States Patent
Arenson et al.

(10) Patent No.: US 6,304,769 B1
(45) Date of Patent: *Oct. 16, 2001

(54) MAGNETICALLY DIRECTABLE REMOTE GUIDANCE SYSTEMS, AND METHODS OF USE THEREOF

(75) Inventors: Ronald L. Arenson, Mill Valley; William V. Hassenzahl, Piedmont; Timothy Roberts, San Francisco, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 28 days.

(21) Appl. No.: 08/951,620

(22) Filed: Oct. 16, 1997

(51) Int. Cl.$^7$ .................................................. A61B 5/05
(52) U.S. Cl. .................................... 600/424; 604/528
(58) Field of Search ................................. 600/424, 411, 600/427, 114, 117, 102, 103, 9, 11–14; 128/899, 897, 898; 604/528, 523

(56) References Cited

U.S. PATENT DOCUMENTS

| | | | |
|---|---|---|---|
| 4,572,198 | 2/1986 | Codrington | 128/653 |
| 5,050,607 | 9/1991 | Bradley et al. | 128/653 |
| 5,188,111 | 2/1993 | Yates et al. | 128/657 |
| 5,202,631 | 4/1993 | Harms et al. | 324/309 |
| 5,273,025 | * 12/1993 | Sakiyama et al. | 600/117 |
| 5,274,551 | 12/1993 | Corby, Jr. | 364/413.13 |
| 5,318,025 | * 6/1994 | Dumoulin et al. | 600/424 |
| 5,323,778 | 6/1994 | Kandarpa et al. | 128/653 |
| 5,386,828 | * 2/1995 | Owens et al. | 600/424 |
| 5,415,163 | 5/1995 | Harms et al. | 128/653.2 |
| 5,433,717 | 7/1995 | Rubinsky et al. | 606/20 |
| 5,447,156 | * 9/1995 | Dumoulin et al. | 600/424 |
| 5,492,122 | 2/1996 | Button et al. | 128/653 |
| 5,513,637 | * 5/1996 | Twiss et al. | 600/424 |
| 5,531,742 | 7/1996 | Barken | 606/21 |
| 5,558,091 | * 9/1996 | Acker et al. | 600/424 |
| 5,572,132 | * 11/1996 | Pulyer et al. | 324/318 |
| 5,577,502 | 11/1996 | Darrow et al. | 128/653.1 |
| 5,592,939 | * 1/1997 | Martinelli | 600/424 |
| 5,603,320 | 2/1997 | Dumoulin et al. | 128/653.2 |
| 5,681,260 | * 10/1997 | Ueda et al. | 600/114 |
| 5,749,925 | 5/1998 | Bocker et al. | 8/436 |
| 5,906,579 | * 5/1999 | Vander Salm et al. | 600/424 |
| 6,059,718 | * 5/2000 | Taniguchi et al. | 600/117 |

OTHER PUBLICATIONS

Bakker et al., (1997) "MR–guided Endovascular Interventions: Susceptibility–based Catheter and Near–Real–Time Imaging Techniques", Radiology 202:273–276.

Bakker et al., (1996) "Visualization of Dedicated Catheters Using Fast Scanning Techniques with Potential for MR–guided Vascular Interventions", Magnetic Reasonance in Medicine 36:816–820.

Baudouin et al., (1992) "Magnetic Resonance Imaging of the Uterine Cervix Using an Intravaginal Coil", Magnetic Reasonance in Medicine 24:196–203.

(List continued on next page.)

Primary Examiner—Brian L. Casler
(74) Attorney, Agent, or Firm—Bozicevic Field and Francis LLP; Carol L. Francis

(57) ABSTRACT

A magnetically directable guidance system useful in, for example, medical magnetic resonance imaging is provided, as well as methods of directing the traverse of a device directable by the remote guidance system to a remote destination. A directable device and methods of use thereof are also disclosed. In one embodiment, the device is a catheter directable using a magnetic resonance imaging system. In another embodiment, the method includes interventional radiological diagnostic and therapeutic procedures.

95 Claims, 8 Drawing Sheets

OTHER PUBLICATIONS

Dumoulin et al., (1993) "Real–Time Position Monitoring of Invasive Devices Using Magnetic Reasonance", Magnetic Reasonance in medicine 29:411–415.

Kandarpa et al., (1993) "Prototype Miniature Endoluminal MR Imaging Catheter", Journal of Vascular Inter. Radiology 4:419–427.

Kawaguchi et al., (1993) "High Resolution MR Images of Bladder Neck Tumors Using an Endorectal Surface Coil", Proc. SMRM, 12th Annual Meeting, 1993, p. 50.

Leung et al., (1995) "Intravascular MR Tracking Catheter: Preliminary Experimental Evaluation", AJR 164:1265–1270.

Martin et al., (1994) "Intravascular MR Imaging in a Porcine Animal Model", Magnetic Reasonance in Medicine 32:224–229.

Martin et al., (1988) "Inflatable Surface Coil for MR Imaging of the Prostate", Radiology 167: 268–270.

Schnall et al., (1989) "Prostate: MR Imaging with an Endorectal Surface Coil", Radiology 172:570–574.

Wildermuth et al., (1977) "MR Imaging–guided Intravascular Procedures: Initial Demonstration in a Pig Model", Radiology 202:578–583.

Gmitro, A.F., et al., 1996, "A real–time reconstruction system for magnetic resonance imaging," *Magn. Reson. Med.* 35(5):734–40.

Jolesz, F.A., and Blumenfeld, S.M., 1994, "Interventional use of magnetic resonance imaging," *Magnetic Resonance Quarterly*, 10(2):85–96.

Lufkin, R.B., 1995, "Interventional MR imaging," *Radiology* 197:16–18.

McKinnon, G.C., et al., 1996. "Towards active guidewire visualization in interventional magnetic resonance imaging," *MAGMA* 4:13–18.

Rubin, D.L., et al., 1990, "Magnetic susceptibility effects and their application in the development of new ferromagnetic catheters for magnetic resonance imaging," *Invest. Radiol.* 25(12):1325–32.

Schenck, J.F., et al., 1995, "Superconducting open–configuration MR imaging system for image–guided therapy," *Radiology* 195(3):805–14.

Stefanadis, C., et al., 1989, "Percutaneous transluminal coronary angioplasty using a steerable guiding catheter: a new technique," *Cathet. Cardivasc. Diagn.* 18(3):187–90.

Stroman, P.W., et al., 1996, "Will it be feasible to insert endoprostheses under MR interventional MRI?" *J. Endovasc. Surg.* 32:396–404.

Ackerman JL, et al. "3D tracking of small rf coils," Fifth Annual Meeting, Society of Magnetic Resonance in Medicine, Montréal, Québec, Aug. 18–22, 1986.

Arenson, RL, "The Practice of Medicine and Radiology n 2020," *Radiology*, 202(2):43A–46A (1997).

Werp, Peter, "Imaging Technology for a Medical Magnetic Guidance System," Invited PaperPersented at the American Physical Society Meeting, Mar. 22, 1996.

* cited by examiner

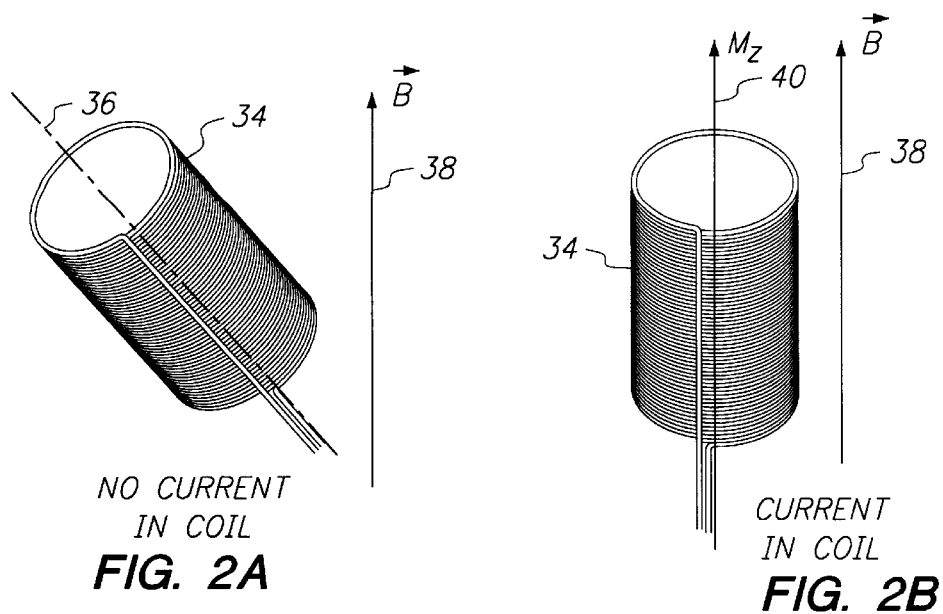
NO CURRENT IN COIL
FIG. 2A
CURRENT IN COIL
FIG. 2B
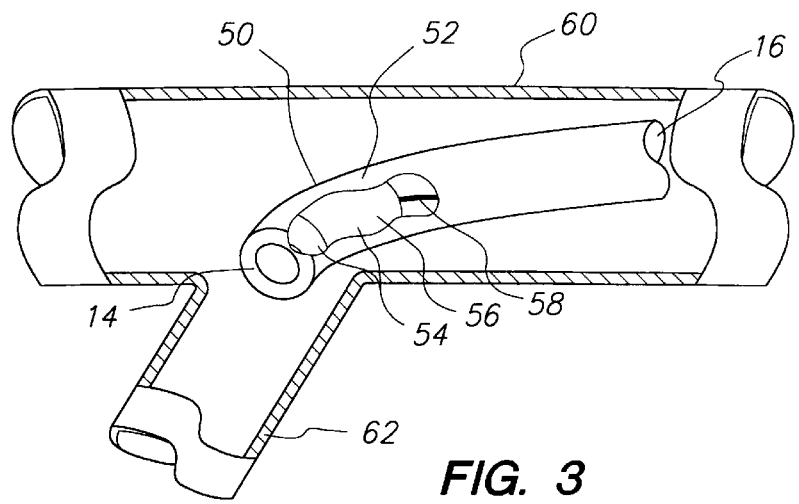
FIG. 3
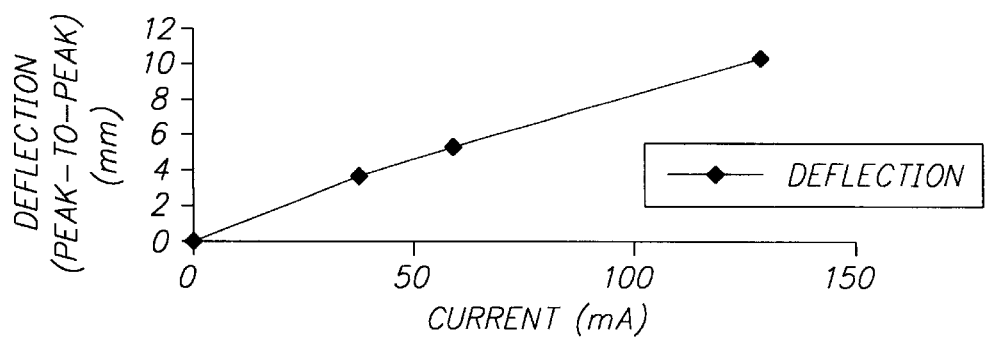
FIG. 11

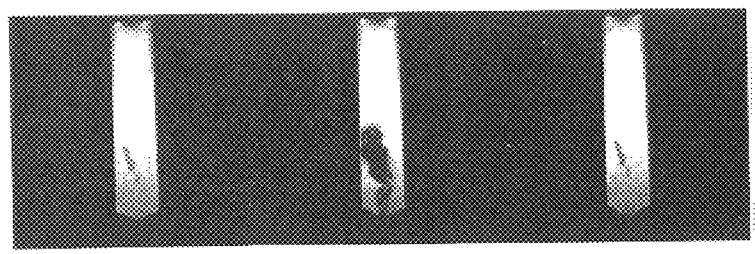
FIG. 6   FIG. 7   FIG. 8
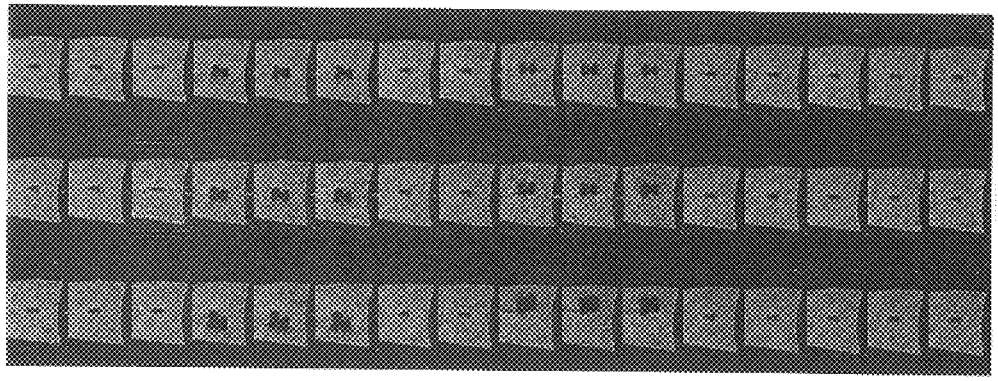
FIG. 9A
FIG. 9B
FIG. 9C

MAGNETICALLY DIRECTABLE REMOTE GUIDANCE SYSTEMS, AND METHODS OF USE THEREOF

TECHNICAL FIELD

This invention relates generally to remote guidance systems. More specifically, the invention relates to magnetically directable guidance systems useful in, for example, medical magnetic resonance imaging and interventional radiological diagnostic and therapeutic procedures. The invention also relates to a method of directing the traverse of a device directable by the remote guidance system, and to methods of use thereof.

BACKGROUND

Interventional radiology uses medical imaging systems such as computed tomography, magnetic resonance (MR), X-ray, and fluoroscopy for therapeutic as well as diagnostic purposes. Healthcare providers use mostly fluoroscopy to visualize a catheter placed within the vasculature of a patient to assist in guiding the catheter to a remote site within the body. Catheters so positioned can be used for injecting a contrast agent to image the vasculature of specific organs, analyzing local chemistries, retrieving samples (e.g., a tissue biopsy), effecting therapeutic procedures such as cryosurgery, delivering a therapeutic agent, blocking of an artery feeding a tumor, or the like. The goal of the procedure is to deliver the working end of a catheter to a specific internal site within the body of the patient.

The vascular system is used to contain the catheter and to act as the conduit along which the catheter progresses. Access to endovascular space is achieved via a puncture with a needle through the skin and through the wall of the vessel, either at the groin or, less frequently, from the axillary area. Typically, a catheter tip is threaded to the destination vessel by manually steering it from the point of entrance, taking advantage of the torque of the relatively stiff catheter with a curve at the tip to enter side branches. The tip of the catheter is advanced by pushing and rotating the catheter at the point of entrance through the skin. The progress of the tip of the catheter within the vascular system is observed on a fluoroscopic monitor when small amounts of radio-opaque contrast material are injected into the bloodstream through the catheter. In addition, guidewires are often used to help pass the catheter, especially in tortuous or sharply angled vasculature.

Although skilled angiographers can reach most destination vessels, the time and effort required to guide the tip of the catheter to the destination vessel, the radiation dose to the patient and staff due to the fluoroscopic imaging required to monitor the progress of the tip of the catheter through the vasculature, the burden of contrast materials introduced into the patient and possible reactions thereto, as well as other complications inherent in the procedure of manually guiding the tip of a catheter, make these procedures difficult and risky. In addition, some vessels cannot be successfully navigated due to the patient's anatomy. Steep angulation of branches or marked tortuosity of vessels can prevent access, especially at the hands of the less-skilled physician.

The position of a catheter in a vessel can be monitored using magnetic resonance (MR) imaging techniques. Briefly, MR imaging is a technique in which an object placed in a spatially varying magnetic field is subjected to a pulse of radio frequency radiation, and the resulting nuclear magnetic resonance signals are combined to give intensity-modulated cross-sectional images of the object. MR imaging systems generally include a large magnet for generating a magnetic field. A patient or object being analyzed is exposed to the magnetic field of the magnet. Hydrogen nuclei (protons) or other biologically significant, nonzero spin nuclei, e.g., $^{31}P$, $^{23}Na$, $^{13}C$, in the magnetic field resonate when exposed to radio waves of a correct frequency. For imaging purposes, the strong uniform magnetic field of the magnet is selectively altered in one or more directions, preferably by small magnetic fields produced by three separate gradient coils associated with the magnet. Current passing through the gradient coils linearly alters the z component of the magnetic field of the magnet in directions controlled by the gradient coils. Signal transmission and reception are produced through use of a radio frequency (RF) transmitter coupled to a transmitting coil or antenna within the imaging unit and an RF receiver coupled to a "receiver coil" also located in the imaging unit. The receiving coil is positioned as close to the patient or object as possible for maximum imaging sensitivity. The patient or object is often surrounded by a body coil that serves both as transmitting and receiving antennae. Alternatively, the body coil can be used as a transmitting antenna only, and a separate surface coil is used as a receiving antenna. The surface coil can usually be placed closer to the tissues or object under examination than a single body coil. An RF oscillator generates radio waves of different frequencies. By controlling the magnetic field in a known way through a switching system that controls the current in the gradient coils, and by generating radio waves of a select frequency, the exact location at which the patient's body or the object is imaged can be controlled. When the frequency of the RF signal is set for the exact value of the magnetic field, resonance occurs. Precession of the excited nuclear magnetic moment leads to induction of small currents in the receiving coil. The induced currents are detected to produce an output signal dependent upon the number of protons involved in the resonance and tissue-specific parameters. The output signal from the RF receiver is processed by a computer system to produce an image display so that the position of the coil can be determined. See, e.g., Brown et al. (1995) *MRI: Basic Principles and Applications* (Wiley-Liss, New York).

Thus, for example, a method for measuring the position of a small RF coil with respect to the coordinate system of an NMR imager has been described in U.S. Pat. No. 4,572,198. Passive tracking of a catheter with near-real-time two-dimensional angiography has also been described. See, e.g., Bakker et al. (1997) *Radiology* 202:273–276; Bakker et al. (1996) *Mag. Reson. Med.* 36:816–820, Kandarpa et al. (1993) *J. Vac. Interv. Radiol.* 4:419–427; Leung et. al. (1995) *Amer. J. Radiol.* 164:1265–1270; Dumoulin, C. L., et al. (1993) *MRM* 29:411–415). In addition, intravascular coils, designed for the vascular imaging of atherosclerotic plaques using a 1.5 T scanner, have been described in Martin et al. (1994) *Magn. Res. Med.* 32:244–249.

However, the ability to use MR imaging techniques to monitor the position of a catheter or other device within the endovascular space of a patient or, for that matter, within a path to any remote destination, does not resolve the difficulty of manually guiding the catheter or device to a destination site that may require, e.g., traversing a tortuous or sharply angled vasculature or other conduit, or guiding the tip of the catheter into small diameter vessels or other branch lines.

Accordingly, there remains a need in the art for a method by which the travel of a catheter or other device to a remote location within endovascular space or along a path to the remote location, can be guided by remote control. In addition, there is a need in the art for an apparatus to effect such a method and to a catheter useful with such a method.

SUMMARY OF THE INVENTION

Accordingly, it is a primary object of the invention to address the above-mentioned need in the art, by providing an apparatus for directing the movement of a directable device.

It is another object of the invention to provide an apparatus for directing movement of a directable device, comprising a substrate wrapped with a steering coil capable of conducting electric current that, when the current is passed therethrough, creates a local directional magnetic moment, a means for applying an electric current through the coil, and a means for generating an external magnetic field to which the a directable device is exposed.

It is yet another object of the invention to provide a method of directing the movement of a directable device. The method comprises providing (i) the directable device comprising a substrate wrapped with a steering coil capable of conducting electric current that when the current is passed therethrough creates a local directional magnetic moment, (ii) a means for applying an electric current through the coil, (iii) a means for generating an external magnetic field to which the directable device is exposed, applying an electric current through the coil, and generating a magnetic field at a strength and frequency, including direct current, sufficient to effect the direction of movement of the directable device.

In one embodiment of the invention, a directable catheter is provided. The directable catheter comprises a flexible elongate tubular substrate having a wall with inner and outer surfaces and a proximal end and a distal end comprising a tip, wherein the tip is intended to be situated in a body cavity, duct or vessel, and a steering coil comprising a conductive metal, wherein the steering coil is capable of conducting electric current that when the current is passed therethrough creates a local directional magnetic moment.

These and other objects, embodiments and features of the invention will become apparent to those skilled in the art upon reading the following disclosure and description of the invention.

BRIEF DESCRIPTION OF THE DRAWINGS

In the course of this description, reference will be made to the attached drawings, wherein like parts denote like parts throughout and wherein:

FIG. 2A illustrates a single solenoidal coil in the presence of external magnetic field B in which no current is passed through the coil.

FIG. 2B illustrates a single solenoidal coil in the presence of external magnetic field B in which current is passed through the coil.

FIG. 3 illustrates a catheter having a sheath surrounding the catheter and coils that has been inserted into a blood vessel of a subject placed in an external magnetic field and in which a current has been applied to the coils thereby deflecting the tip of the catheter to allow direction of the catheter into a branch vessel.

FIG. 6 is a visual image of a 25–30 turn coil wound on a 1.2 mm former, using 36-gauge insulated copper wire. Images were obtained from a 2 T CSI-Omega scanner and 55 mm i.d. birdcage transmit/receive RF coil. A coronal image before current application is shown.

FIG. 7 is a visual image representing one of many conceivable configurations of a 25–30 turn coil wound on a 1.2 mm former, using 36-gauge insulated copper wire. Images were obtained from a 2 T CSI-Omega MR scanner and 55 mm i.d. birdcage transmit/receive RF coil. The image was taken during application of about 10 mA direct current. Clear field disturbances are generated leading to signal voiding extending well beyond the physical coil.

FIG. 8 is a visual image of a 25–30 turn coil wound on a 1.2 mm former, using 36-gauge insulated copper wire. Images were obtained from a 2 T CSI-Omega scanner and 55 mm i.d. birdcage transmit/receive RF coil. The image was taken after current shutoff documenting that the voiding artifact disappears.

FIG. 9A is a row of consecutively obtained images corresponding to a dynamic series of 0, +38 mA, 0, −38 mA, and 0 current applied to a coil as described in Example 3.

FIG. 9B is a row of consecutively obtained images corresponding to a dynamic series of 0, +58 mA, 0, −58 mA, and 0 current applied to a coil as described in Example 3.

FIG. 9C is a row of consecutively obtained images corresponding to a dynamic series of 0, +130 mA, 0, −130 mA, and 0 current applied to a coil as described in Example 3.

FIG. 11 is a plot of the peak-to-peak displacement, i.e., the range of displacement corresponding to + and − current, of the catheter tip as a function of applied current.

DETAILED DESCRIPTION OF THE INVENTION

Figure 1A:
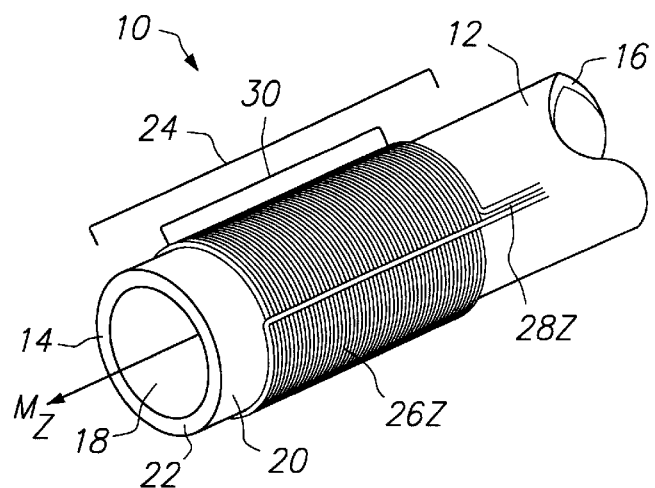
FIG. 1 illustrates a catheter tip having a coil with a magnetic axis parallel to ($M_z$, FIG. 1A) or perpendicular to ($M_x$, FIG. 1B; $M_y$, FIG. 1C) the longitudinal orientation of the catheter tip.
FIG. 1D illustrates a catheter tip having overlying inner, medial, and outer coils with magnetic axes that are mutually orthogonal, in which the medial and outer coils are cut away for illustrative purpose.
FIG. 1E is a cutaway illustration of a catheter tip having a sheath surrounding the catheter and the overlying inner, medial and outer coils.

Before the apparatus and methods of using the apparatus are described, it is to be understood that this invention is not limited to the particular MRI equipment, methods, catheters, or therapeutic interventions described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "and", and "the" include plural referents unless the contexts clearly dictate otherwise. Thus, for example, reference to "a magnet" includes different types and large numbers of such, reference to "an MR imaging system" includes one or more machines, methods or steps of the type described herein, reference to "a coil" includes one or more coils, and the like.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention.

Definitions

In describing and claiming the present invention, the following terminology will be used in accordance with the definitions set out below.

The term "deflection" is defined as displacement from an otherwise straight-line path induced, for example, by an electrostatic or electromagnetic field.

The terms "treatment," "treating," "treat" and the like are used herein to generally mean obtaining a desired pharmacologic, surgical, radiologic, and/or physiologic effect. The effect may be prophylactic in terms of completely or partially preventing a disease or symptom thereof and/or may be therapeutic in terms of a partial or complete cure for a disease and/or adverse effect attributable to the disease. The term "treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The term "therapeutic intervention" is defined as a means relating to the treatment of a disease or disorder by remedial agents or methods. Some therapeutic interventions useful in the invention include, but are not limited to, cryosurgery, hyperthermia treatments, the introduction of radionucleotides or any form of energy, the introduction of stents, balloon or coil placement, the procurement of biopsies, the administration of a pharmacologic agent, and the like.

An "external magnetic field" is a magnetic field that is generated by a magnet physically separate from the directable device and which, upon application of a current to a coil applied to the device, results in a torque that guides the direction of the device as the magnetic moment attempts to align with the external magnetic field. "Radio frequency energy" or "RF energy" is electromagnetic energy in the range from about 10 kilohertz to about 100 gigahertz. For MRI, frequencies in the range of about 8 to 85 MHz are typically used.

The invention relates to an apparatus and a method for guiding the direction of a directable device to a desirable location in, for example, a subject's body, other remote location that is difficult or hazardous to access otherwise, or the like. The apparatus comprises the directable device which, in turn, comprises a substrate wrapped with a coil capable of conducting electric current, a means for applying an electric current through the coil, and a means for applying an electric current through the coils and a means for generating a magnetic field external to the directable device and to which the directable device is exposed. When current is passed through the coil a local directional magnetic moment is created. Under the influence of the external magnetic field, the generation of the magnetic moment results in a torque that guides the direction of the device as the magnetic moment attempts to align with the external magnetic field.

The term "coil" as used herein intends a number of turns or fractions of turns of a conductive material, such as a wire, ribbon, or any other physical form of conductive material that can be, for example, formed into a current loop and used to produce a magnetic moment sufficient to cause a deflection in the direction of motion of the substrate to which the coil is applied. Such a coil is referred to herein as a "steering coil." Alternatively, an "RF coil" may be used to produce or receive radio-frequency (RF) signals. The term "coil" encompasses such physical forms as solenoidal coils, spiral coils, helical coils, Helmholtz coils, birdcage coils, and the like. A coil may be formed in situ on a substrate by any conventional method, e.g., wrapping, winding, layering, and the like, preformed and transferred to the substrate, or applied directly to the substrate by a photolithographic or other similar technique. Alternatively, a coil may be preformed and transferred to the desired substrate. The terms "wrapped," "incorporated," and "applied" when used to refer to the placement of a coil on a substrate are intended to encompass any method or configuration by which the coil is formed or placed onto the substrate, unless the context clearly dictates otherwise.

The substrate can take the form of, for example, an elongate, flexible tube, e.g., a catheter, or solid, semi-solid or hollow object of any shape such that (a) a coil may be formed thereon, (b) the direction of movement thereof may be guided by passing current through the coil and exposing the object to an external magnetic field, and (c) is of an appropriate size and shape to traverse or be caused to traverse a path to the desired remote location.

An elongate substrate may be, for example, a catheter, a guide wire (either ferrous or nonferrous), an optical fiber, or the like. A substrate in the form of an elongate tube or cylinder generally comprises a distal end and a proximal end. The distal end further comprises a tip. Typically, a steering coil is incorporated into the tip of the elongate substrate to allow deflection of the tip, and therefore guidance of the direction of the elongate substrate, upon application of a current to the steering coil and exposure of the device to an external magnetic field. The substrate is made from a material selected to have sufficient flexibility to permit the tip of the substrate to be deflected when, under the influence of an external magnetic field, the magnetic moment, generated from application of a current through the coil, and the resultant torque, attempts to align with the external magnetic field. Preferred substrate materials have a low modulus of elasticity in the range of about 0.1 to 20 MPa, more preferred materials in the range of about 5 to 15 MPa, and even more preferred in the range of about 5 to 10 MPa. Most preferred materials have a modulus of elasticity of about 7 MPa. The elongate substrate is intended to be inserted into a point in the path or conduit by which the remote site may be accessed, and manually, mechanically, by self-propulsion, or otherwise advanced toward the desired remote destination. The proximal end of the elongate substrate thus forms a means by which to advance the tip of the substrate and/or a means by which the substrate is tethered and retrieved when the remote placement of the tip, and any other desired activities once the tip has been placed, have been accomplished. The apparatus is used to guide the direction of the tip of the substrate to allow control over the route the tip is intended to take to reach the remote site.

Examples of remote sites to which such an elongate substrate may be advanced, and by which traverse of the route is accomplished by guiding the direction of the substrate as described herein, include remote sites in a subject's body, such as the brain, the heart, a tumor, a compromised site within the vasculature, i.e., a site of hemorrhaging or of an aneurism, and the like. The apparatus may also be used in nonbiomedical applications, e.g., to place or remove radioactive materials in remote locations such as nuclear reactors.

A substrate in the form of a solid or hollow object of other shape is intended generally to be advanced by manual manipulation or, e.g., self-propulsion, mechanical means, or the like, depending on the application. Thus, for example, if such a device were to be inserted into a subject's body, advance of the substrate may be accomplished by being carried along with flow of blood, or by a mini-mechanical propulsion system. Means by which such a substrate may be advanced toward the remote site include mechanical means well known in the art. In this embodiment, the substrate may be tethered to permit its retrieval when and if desired. The tether may be in the form of lead wires to the coil or any other manner of tether such that retrieval of the substrate may be accomplished. The tether may also be releasable from the substrate to allow placement of the substrate in a desired location in the subject's body, preformed item of manufacture, or the like. Such a substrate may be any material suitable for the intended use, e.g., insertion into a subject's body or traverse of a path to any desired remote location. Thus, for example, a substrate intended to be placed in a site upon release of the tether and to deliver a sustained release therapeutic agent formulation to a desired local site may be a bioerodible polymer. Such polymers are well know in the art. A device intended to be guided into a hazardous situation, e.g., into a fire, must be able to withstand the conditions of the situation as required.

In order to guide the direction of the device, a steering coil is applied to the substrate of the device. Current is passed through the steering coil to create a magnetic moment. The amount of current that must be passed through the coil to create a magnetic moment sufficient to guide the direction of the substrate depends not only on the flexibility and/or dimensions of the device, and/or the substrate, but also on the strength of the external magnetic field. For a given substrate, then, the amount of current required to be passed through a steering coil is inversely proportional to the strength of the external magnetic field. Generally, magnetic field strength ranges from a lower strength of about 0.05 T to 0.5 T to an upper strength of about 1.5 T to 7.0 T, but both lower and higher strengths may be utilized.

The lower range of magnetic field strength is typically limited by the amount of current that can be applied to the coil in a given application. As is well known in the art, increasing the current in the coil can result in the generation of heat. If, for a given external magnetic field strength, the current required to create a sufficient force to guide the direction of the substrate would generate heat that is incompatible with the application, i.e., proximity to sensitive electrical devices or live tissue, the coil can be insulated to minimize heat transfer. Alternatively, the coil can be jacketed to allow a heat exchange material, e.g., water, to be passed over the coil. When the substrate is an elongate tube or hollow object, the heat exchange material may be passed through the tube or hollow object.

The external magnetic field can be generated by any device capable of generating a magnetic field of sufficient strength to effect guidance of the direction of the device for a given current applied to the steering coil. Thus, the magnetic field may be generated by a magnet, generally of three types: permanent, resistive, and superconduction. In one preferred embodiment, the magnetic field is generated by a magnetic resonance imaging apparatus.

In order to guide the movement of the substrate to the remote location in an object or subject, the substrate can be visualized by any of well-known techniques. Thus, the substrate may be localized using x-ray fluoroscopy, using an optical fiber imaging system, or by generating an image using the transmitting coil or antenna and the receiving coil located in an MR imaging unit. Alternatively, the position of the substrate may be tracked using a "receiver coil" applied to the substrate as an antenna. The receiver coil may be the same coil used to create the magnetic moment by which the direction of the substrate is guided, i.e., a steering coil, or another independent coil may be applied to the substrate. The use of a receiver coil applied to a substrate to image the substrate is described in U.S. Pat. No. 5,050,607 to Bradley et al., Dumoulin et al. (1993) *Magn. Reson. Med.* 22:411–415, Leung et al. (1995) *AJR* 164:1265–1270, and Wildermuth et al. (1997) *Radiology* 202:578–583.

In addition, the device can be guided along a route to a remote location by incorporating an RF "transmit/receive coil" into the substrate that may be used to provide an image of the structure of the local environment. The RF transmit/receive coil may be a steering coil, or another independent RF a transmit/receive coil may be applied to the substrate. Basically, the imaging method involves applying a magnetic field gradient across the object or subject into which the device has been inserted, e.g., using an MR imaging apparatus, pulsing RF energy through the RF transmit/receive coil applied to the substrate and "listening" to the return signal from the local environment using the RF transmit/receive coil as an antenna. The signal emanating from the local protons, or other nuclei, excited by the RF energy is frequency and phase encoded to store spatial proton distribution, which can be revealed by appropriate transformation, e.g., Fourier transformation, using standard MRI methods. The output signal from the RF transmit/receive coil is processed by a computer system until an image of the desired local environment is produced. The close proximity of the RF transmit/receive coil to the local environment results in generation of an image with spatial resolution superior to that which can be achieved using an external coil. In this manner, the location of small branch points can be resolved and the direction of the device more precisely guided in order to enter the branch point. Such local environment imaging methods are well known in the art and are described, for example, in: Martin et al. (1994) *MRM* 32:224–229; Kawaguchi et al. (1993) *Proc. SMRM, 12th Annual Meeting,* 1993, p. 50; Baudouin et al. (1992) *Magn. Reson. Med.* 24:196–203; Schnall et al. (1989) *Radiology* 172:570–574; and Martin et al. (1988) *Radiology* 167:268–270.

In one embodiment, then, the present invention relates to a device comprising a catheter. The catheter has a tip that can be "aimed" or directed within the vasculature or other conduit system of a subject by generating a magnetic moment at the tip of the catheter, i.e., a magnetic moment produced by an electric current in a steering coil. The spatial and temporal characteristics of the moment are sufficient to deflect the catheter tip so that it can be moved in a desired direction.

The invention, together with additional features and advantages thereof, may be best understood by reference to the following description taken in connection with the illustrative drawings.

With reference to FIGS. 1A, 1B, 1C, 1D, and 1E, a directable catheter (10) is generally provided. The directable catheter comprises a flexible elongate tube (12) having distal end (14), proximal end (16), inner surface (18), outer surface (20) and, between inner surface (18) and outer surface (20), wall (22). The length of the catheter from proximal end to distal end may be 2 meters or more. Distal end (14) has tip (24) that comprises coil (26) and, extending from coil (26), leads (28) that are electrically connected with an instrument capable of electrical communication with the coil. Coil (26) has a length (30) measured along the longitudinal axis of tube (12).

The material from which substrate of the elongate tube (12) is made must be flexible, i.e., must have a modulus of elasticity in the range as described above. The elongate tube used in the subject catheter invention is typically small, having a tip diameter in the range of 1–5 French. Smaller catheters provide access to smaller vessels and are more easily guided using a smaller applied current and a low field MR system.

The conductive material from which coil (26) is made may be any conductive material, such as stainless steel, copper, gold, silver, or an alloy thereof. Copper, which has a low resistivity, is a preferred conductor for most applications. Coil (26) at catheter tip (24) may be embedded in catheter wall (22) or may be wrapped or otherwise placed on inner wall (18) or outer wall (20). Coil (26) may be made from insulated or noninsulated conductive material. If non-insulated conductive material is used, the coil-wrapped catheter tip is preferably enveloped in a sheath (32) (see FIG. 1E).

Figure 1B:
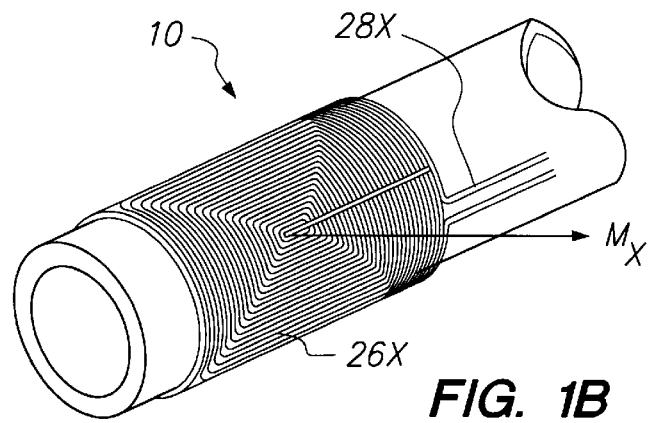
Figure 1C:
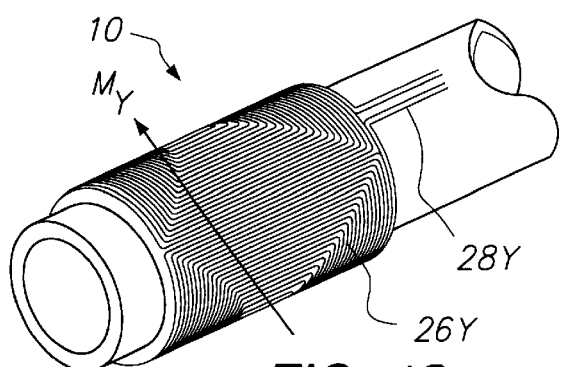

Catheter tip (24) may be wrapped with one or more coils (26) in any configuration that results in the formation of a magnetic moment when current is passed through leads (28) to the coil. As depicted in FIG. 1A, coil $(26_z)$ may be a solenoidal coil wrapped on catheter tip (24). Such a coil produces a magnetic moment $M_z$ when a current is passed therethrough. Alternative coil configurations are depicted in FIGS. 1B and 1C. Coils $(26_x)$ and $(26_y)$ in FIG. 1B and FIG. 1C, respectively, are concentric coils having a square or rectangular configuration. This configuration is not intended to be limiting; a circular, i.e., spiral pattern configuration could be used, or an elliptical, triangular, or any other geometric configuration that, when a current is passed through the coil, results in a magnetic moment having the desired orientation.

Other configurations by which the coil may be wrapped are Helmholtz or modified Helmholtz coils, or any other configuration known in the art by which a magnetic moment having the desired orientation may be produced.

Length (30) of coil (26) will vary depending on a number of factors including, for example, the material, and modulus of elasticity thereof, from which tube (12) is made, the dimensions of tube (12) such as the inner diameter, outer diameter and the thickness of wall (22), the intended use of catheter (10), e.g., whether the tip is intended to be negotiated through a tortuous vasculature thus requiring greater flexibility of the tip to allow for maximal deflection, the MR field strength, and the like. Very small coils may be used in the invention; coils as small as 0.05 mm inside diameter and 0.5 mm in length have been used. Typical coils that are used are, however, 0.4 mm inside diameter, 3 to 4 mm long, and use 0.05 mm diameter copper wire.

Figure 1D:
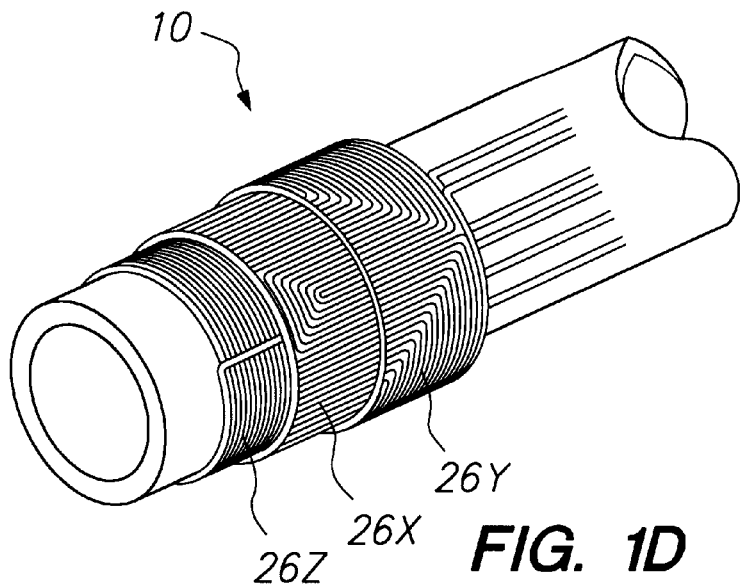
Figure 1E:
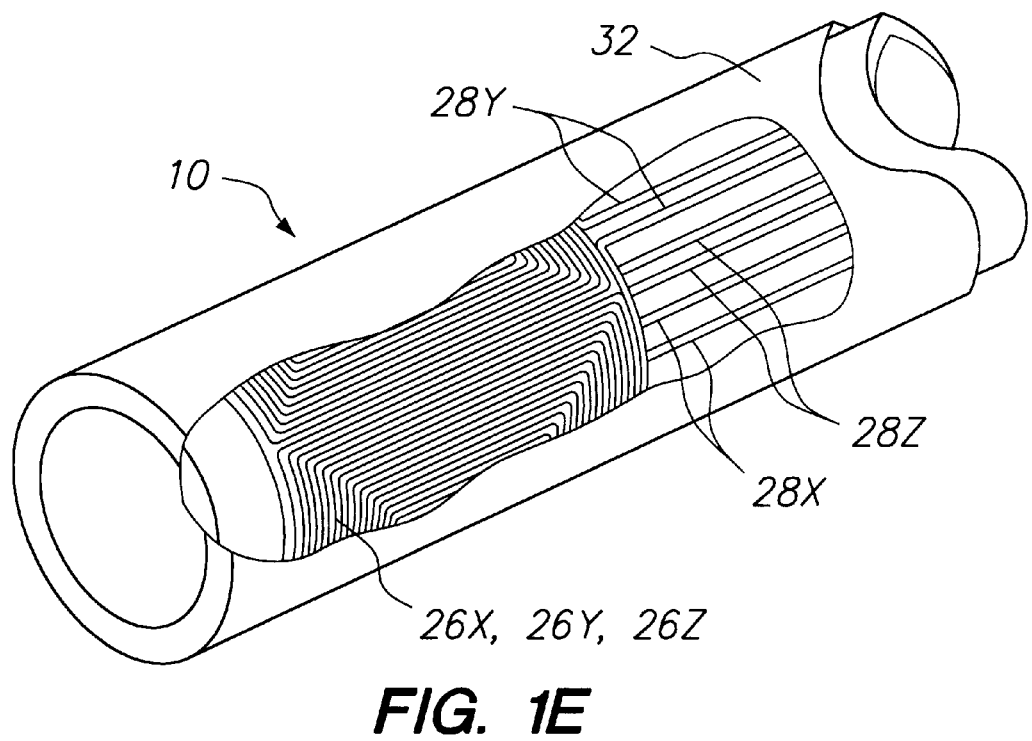

The number of coils (26) wrapped onto the catheter also depends on similar factors. Thus, as shown in FIGS. 1A, 1B and 1C, one coil may be applied to catheter tip (24). Preferably, coils $(26_x)$, $(26_y)$ and $(26_z)$ will be applied to the tip of the catheter. Although the coils may be placed end-to-end along the longitudinal axis of tube (12), it is preferred that the coils are layered as inner, central and outer coils. As depicted in FIG. 1D, coil $(26_z)$ is the inner coil, $(26_x)$ is the central coil, and coil $(26_y)$ is the outer coil, however, any order of the coils as inner, central and outer coil may be used. In addition, inner, central and outer coils may be separated by an insulating material. When two or more coils are present, an alternate configuration includes, for example, a co-planar configuration of a coil having multiple, independently activatable circuits, in which activation of a selected circuit within the coil results in the desired magnetic moment or moments.

When all three coils are present they are preferably configured so that magnetic moments $M_x$, $M_y$, and $M_z$ are mutually orthogonal. The lengths of coils $(26_x)$, $(26_y)$ and $(26_z)$ may be the same or different. It is preferred that the coils are applied to outer surface (20) of the catheter. Other configurations are possible, however, this configuration is generally preferred because it allows the catheter core to remain free for the delivery of materials for diagnostic or interventional actions by the operating physician. The coil configuration depicted in FIG. 1D also produces a large magnetic moment while using a small quantity of conductive material and, thus, producing a minimal quantity of heat.

Furthermore, any of coils $(26_x)$, $(26_y)$ and $(26_z)$ may serve as an RF antenna or "receiver coil" or as an RF transmit/receive coil. Alternatively, a separate coil may be applied to the substrate to serve as a receiver coil and/or a transmit/receive coil. The presence of a receiver coil and/or a transmit/receive coil is one preferred embodiment of the invention because, to find the orifice of a very small vessel, enhanced visualization of the vessel must be achieved. Current MR systems, even high field MR systems, generally do not have sufficient resolution to see vessels of less than a diameter of approximately 3 mm. Thus, one or more coils are applied to the catheter tip which acts in a manner analogous to a surface coil in an MR system, allowing visualization of the local environment of the tip, e.g., small orifices. In one configuration, the receiver and/or transmit/receive coil can be attached to a special catheter or guide-wire that can be positioned just inside the tip or even beyond the steering coils, and is powered through wires in the internal catheter. These coils would most likely be used as a receiver only. Alternatively, the receiver and/or transmit/receive coils can be permanently fixed at the tip, possibly using the maneuvering coils themselves.

Directional guidance and imaging can be carried out simultaneously, or alternatively, by rapidly switching between the steerage, i.e., delivery of current to the steering coils, and the transmit/receive coil, i.e., sending and/or receiving RF signals to the imaging, modes of the invention. Further, both directional guidance and imaging can be effected using two entirely different means. Specifically, imaging can be obtained via the MR signal and also by using light and optics in the catheter. Directional guidance is obtained by use of the MR scanner field and/or by manual movement via a guide-wire or a similar means.

As mentioned above, FIG. 1E is a cutaway drawing illustrating catheter (10) comprising elongate tube (12) having tip (24) on which is placed coils $(26_x)$, $(26_y)$ and $(26_z)$ and leads $(28_x)$, $(28_y)$ and $(28_z)$, respectively. The tip of the catheter is covered with sheath (32). The purpose of the sheath is, for example, to minimize the interaction between the electrical elements of the catheter and the body fluid or tissue into which it is intended to be placed. As with the material used for elongate tube (12), the material used for sheath (32) may be any material suitable to serve the desired purpose of the sheath. In addition, the sheath is made from a material that will not interfere with the steering of the catheter tip. Preferably, the sheath is made from a material that has a modulus of elasticity that is the same as or less than that of the substrate from which the catheter is made.

An important aspect of the invention is that the magnetic field in the MR system can be used to precisely maneuver a catheter into a desired vessel, body cavity or duct. The tip of the catheter can be deflected in a desired direction by altering the orientation of the magnetic moment produced by the coils at the tip of the catheter. The magnetic moment can be adjusted by altering the current supplied independently to the coils.

A coil is "activated" by passing an electric current through leads (28) and coil (26) from any power source known in the art. In one embodiment, leads (28) are physically connected to an instrument capable of generating the required current to the coils. When coils ($26_x$), ($26_y$) and ($26_z$), are present, each coil may be independently activated by three separately controllable currents or simultaneously activated in any combination of two or three of the coils.

Electrical energy may be delivered to an electronic circuit in the catheter by the RF field used for MR imaging The requisite micro-circuitry, providing the equivalent of capacitors and switches, is well known in the art and can be built into the catheter to generate charge sufficient, when discharged, to activate the coils. This circuit may be located a short distance, e.g., 2 to 10 cm, from the tip of the catheter. Switches can be selectively activated by coding signals in RF pulses transmitted from the MR system to turn on, off, and adjust the current applied to the coils. These RF pulses may require minor changes to the MR system RF generators that would be within the skill of the art.

As described in greater detail in the following examples, tip (24) of catheter (10) is "aimed," "guided," "directed," "oriented" or "steered" by applying a current to coil (26). This results in the production of a magnetic moment, which has an axis that is a function of the configuration of the coil. When under the influence of an external magnetic field, the generation of a magnetic moment results in a torque that twists the tip of the catheter as the magnetic moment attempts to align with the external magnetic field. This is illustrated in FIG. 2. FIG. 2A illustrates a single solenoidal coil (34), having axis (36), through which. no current is being passed, in the presence of a external field B (38). FIG. 2B depicts coil (34) through which a current is being passed, thereby resulting in magnetic moment $M_z$ (40), and which has aligned with the external magnetic field B (38). In a similar manner, tip (12) of catheter (10) having coil (26) is deflected due to the interaction of the magnetic moment produced by the coil in the tip and the applied external magnetic field.

FIG. 3 illustrates catheter (50) that has been inserted into a branched blood vessel (60) of a subject placed in an external magnetic field. Catheter (50) comprises sheath (52), elongate tube tip (54), coils (56) and leads (58). Application of currents to coils (56) results in deflection of tip (54) to allow direction of catheter (50) into branch vessel (62).

A variety of means may be used as an input device to control the tip deflection by continuously selecting and adjusting the current supplied to the coil. A standard joystick provides X and Y guidance. Three-dimensional guidance can be achieved with this two-dimensional system by having the system monitor the tip orientation relative to the axis of the catheter. Alternatively, the two-dimensional control can be converted into X, Y and Z signals either with a modified joystick or by altering the currents to the coils based on the catheter tip position relative to the MR system magnetic field orientation. The modified joystick could be simply the use of a joystick having a button that could control deflection of the tip of the catheter in the third dimension. Other possible input devices include "virtual reality" gloves or external light/photodetector systems to follow hand motion.

The catheter can further comprise a means for providing a therapeutic intervention, so that once the catheter reaches the desired destination, a treatment process can be initiated. Guidance of the catheter to an area where treatment is desired thus provides important access to remote anatomical locations which are currently difficult to access or are inaccessible.

One potential use is the deployment of balloons or the use of coils to treat hemorrhage, aneurysms, or to cut off vascular supply to tumors and arteriovenous malformations (AVMs). Such coils are well known in the art and are described in, for example, U.S. Pat. No. 5,643,254 to Schaller et al., U.S. Pat. No. 5,522,836 to Palermo, U.S. Pat. No. 5,354,295 to Guglielmi. Additionally, devices could be incorporated into a catheter whereby the catheter can be used to maneuver into tumor masses, perhaps to be lodged in the cells of the tumor, after which heat or cold are provided in an amount and over a time period sufficient to kill the tumor cells. The kill zone can be monitored using standard MR techniques. Similarly, radioactive needles can be implanted into otherwise inaccessible neoplasms.

Different component parts can enhance the use of the invention. For example, small stents can be utilized to prevent emboli, formation of plaques or to open small branches of vessels such as the coronary, internal carotid, or vertebral arteries. Special biopsy needles can be created to sample tissue through the wall of small vessels. The biopsy needle will be angulated from the axis of the catheter, and clotting devices can be used if the damage to the vessel wall is substantial.

The catheter guidance system can also be used to introduce current, such as can be used for the diagnosis and treatment of cardiac arrhythmias, or for the triggering and analysis of epileptic seizures. Alternatively, the currents can be used to heal wounds such as non-union fractures.

Alternatively, radiation can be delivered through the catheter system using a system which delivers a controllable dose of radiation to a vessel, e.g. by implanting a radioactive compound in a tumor. The radiation treatment can be designed for tumor destruction or for preventing restenosis after angioplasty (see U.S. Pat. Nos. 5,616,114 and 5,618, 266).

Figure 4:
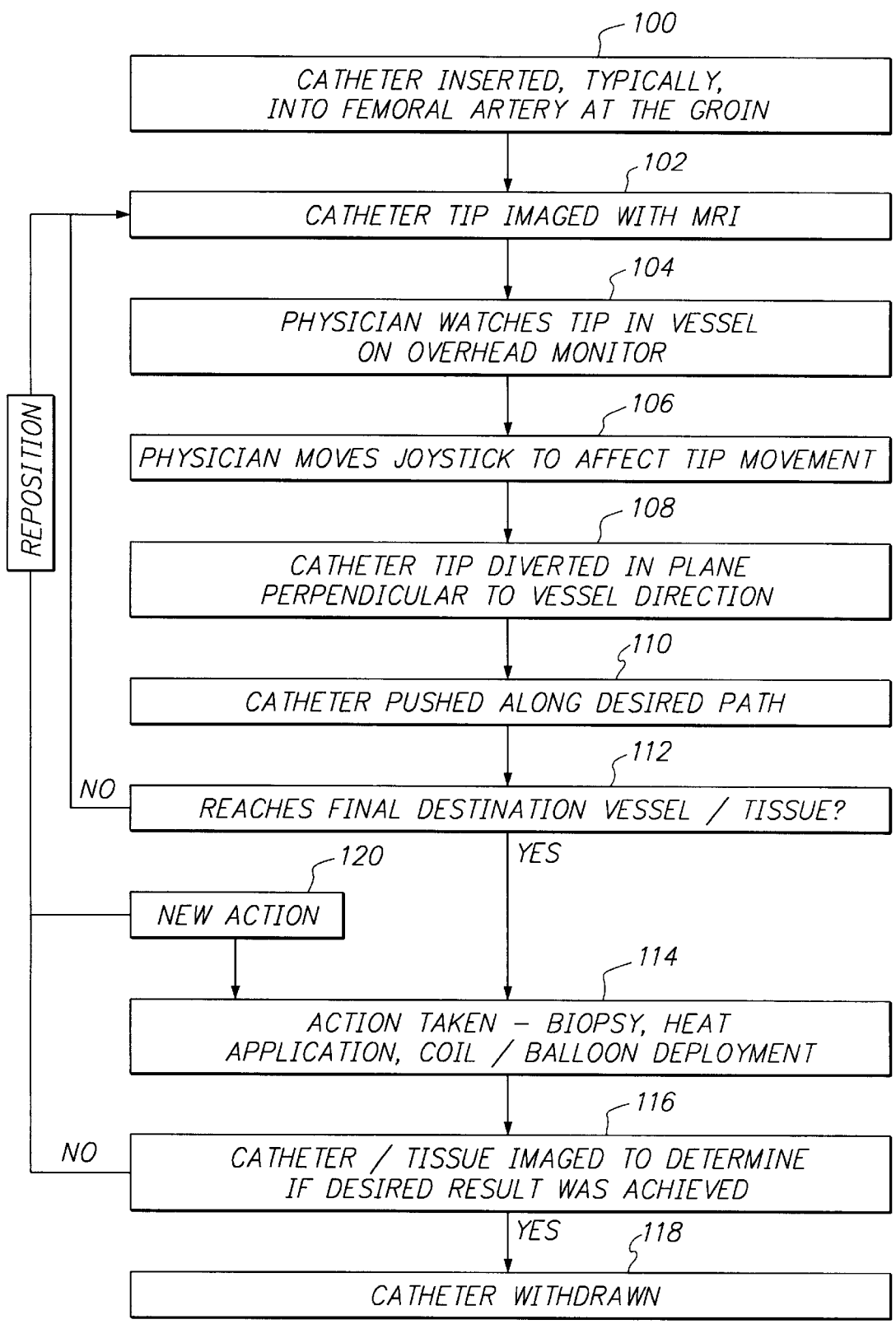
FIG. 4 is a block diagram of a method for guiding a catheter to a remote location in a subject according to one embodiment of the present invention.

With reference to FIG. 4, a flow chart is provided illustrating the steps used in conjunction with the invention. Basically, a catheter is inserted into a subject, guided to a remote location, where a desired action is taken using the catheter, and the catheter is withdrawn. In step 100, a catheter having coils for guiding the direction of the tip of the catheter is inserted into a patient prepared to undergo an interventional radiological diagnostic and/or therapeutic procedure. As described above, the coils at the tip of the catheter are coupled to a means for applying a current to each coil under control of a computer and a joystick interface. The catheter has a proximal end that is exposed to allow the operating physician to manually manipulate the tip of the catheter along a desired path.

The catheter is inserted under local anesthesia into a blood vessel of the patient. Typically the site of insertion is the femoral artery at the patient's groin. In step 102, the tip of the catheter is imaged, preferably with MRI, while in step 104 the operating watches the image of the tip in the patient's blood vessel.

In step 106, the physician moves the tip of the catheter using the joystick. The tip of the catheter may, as exemplified in step 108, be in a plane perpendicular to the longitudinal axis of the vessel. In step 110, the physician manually manipulates the proximal end of the catheter to advance the tip of the catheter along the desired path. If the tip of the catheter is thereby situated at the destination vessel or tissue, step 112, the desired interventional diagnostic or therapeutic action is taken, step 114, e.g., electrocautery, cryosurgery, biopsy sampling, direct therapeutic agent delivery, delivery of therapeutic agent-delivery device, e.g., a bioerodible polymer drug formulation, coil deployment, balloon deployment, and the like. On the other hand, if the final destination for the catheter tip has not yet been reached, the process is repeated beginning at step 102.

In step 116, the tip of the catheter is again imaged, as is the vessel or tissue that is the object of the interventional procedure, to determine whether the desired result was achieved. If the desired result was achieved, the catheter is withdrawn in step 118. If the desired result was not achieved, at least two choices are available to the physician. The action can be repeated or, as indicted in step 120 a new action taken. Alternatively, the catheter tip can be repositioned by repeating the process beginning at step 102.

Figure 5:
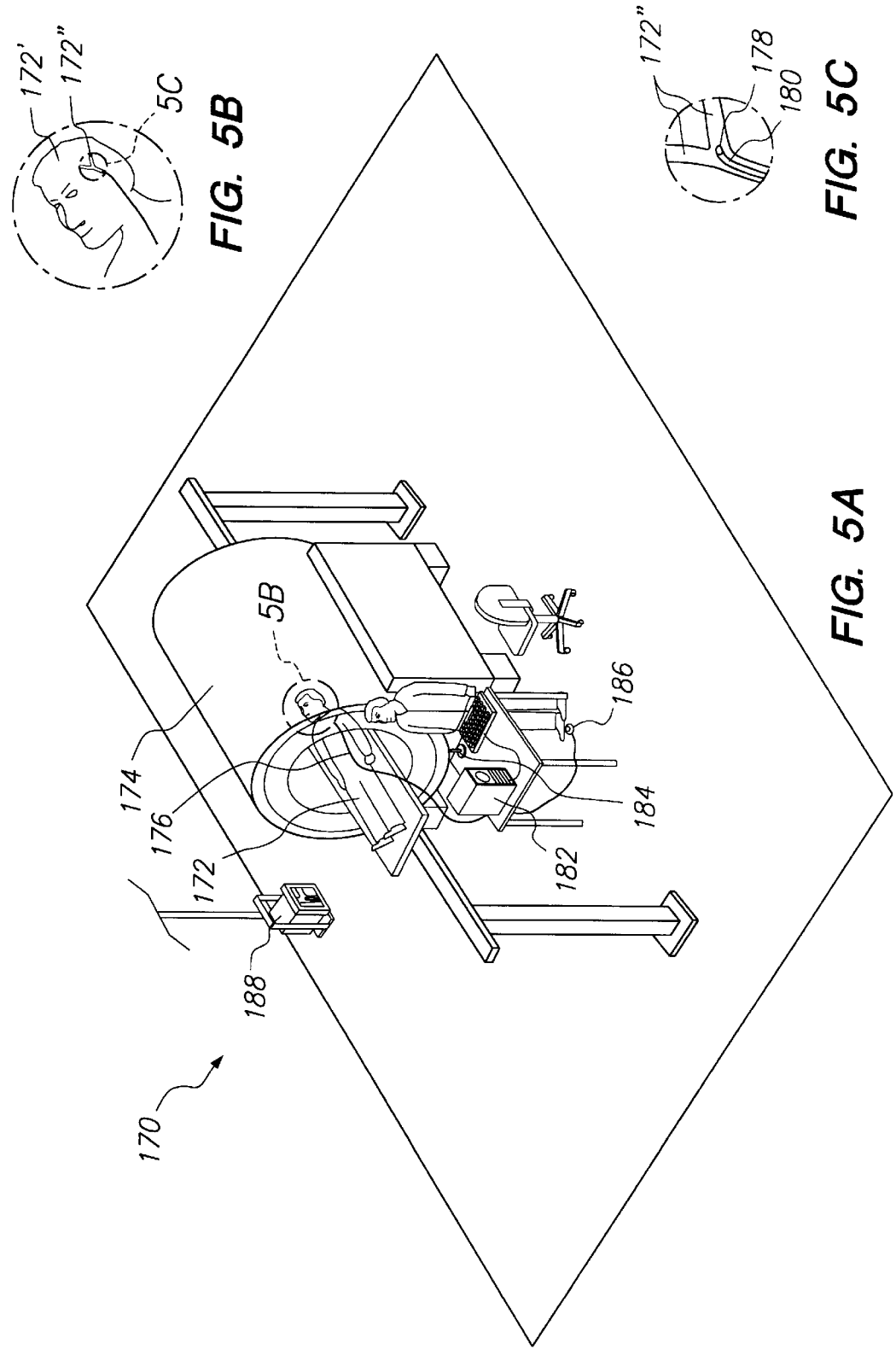
FIG. 5 is an illustration of a system suitable for implementing a method of guiding a device to a remote destination in accordance with one embodiment of the invention.

FIG. 5A illustrates one embodiment of an apparatus suitable for implementing the method described in the flow chart of FIG. 4, which is shown generally at (170). Patient (172) is situated within a magnetic resonance imaging system (174). An expanded view of the patient's head (172') and the vessels (172") within is shown in FIG. 5B. A further expanded view of the vessels (172") within the patients' head is shown in FIG. 5C.

MR systems typically used for direct surgical techniques are low-field strength instruments capable of producing a magnetic field strength in the range of about 0.2 Tesla or 0.5 Tesla. These low-field MR systems are used to gain space in which a physician can operate in the useful portion of the magnetic field. By contrast, for endovascular techniques the operating physician is usually positioned at the patient's groin and manipulates the catheter at the site of puncture. In this situation, high-field strength MR systems, e.g. about 1.5 Tesla or greater, can be utilized. Such systems typically provide better visualization and more rapid imaging. Furthermore, for a given steering current, the torque on the catheter is proportional to the field strength. This invention can also be used in low field MR systems which are less expensive and widely deployed. In addition, these low field systems often offer better access to the patient, which would be especially important for nonvascular applications. This method can also be used with other magnetic field diagnostic or therapeutic systems.

A catheter (176) as described and claimed herein has tip (178) which has been inserted into patient (172) and advanced into the vessels (172") of patient's head (172'). Tip (178) comprises sheathed coils (180). Leads (not shown) from coils (180) extend the length of catheter (176) and are connected via computer (82) to a means for applying current to the coils. Computer (182) is used to control the current applied to coils (180), and synchronize with the RF signals applied to and/or received from a transmit/receive coil. This computer is interfaced to the computer for the MR system or suitable control systems could be incorporated into programs in the MR computer. Joystick (184) is used to control the tip deflection by continuously selecting and adjusting the current supplied to the coils as described above. Footpedal (186) is used to activate the simultaneous or switched MRI imaging mode and catheter tip direction guidance mode. Display screen (188) is used to observe the images created by the MRI apparatus, to monitor progress of the catheter (176) as it is guided through the patient's endovascular space to the vessels (172") in the patient's head (172'), and/or to display the images generated by the RF coil.

An advantage of this embodiment of the invention is that the one MR system is used for both imaging the area of interest and guiding a catheter to the area of interest. An additional advantage is that the same catheter can be used for imaging a local environment and for delivering a therapeutic intervention. A further advantage of the invention is that the catheter can be designed to deliver a range of different treatments. These treatments include, but are not limited to, cryosurgical intervention, hyperthermia or hypothermia probes, shunt placement, biopsy procurement, and the like. Such methods are well known in the art. For example, means for MRI-assisted cryosurgery is described in U.S. Pat. No. 5,433,717 to Rubinsky et al. and U.S. Pat. No. 5,531,742 to Barken, hyperthermia probes are described in U.S. Pat. No. 5,323,778 to Kandarpa et al. and U.S. Pat. No. 5,492,122 to Button et al., the disclosures of which are incorporated herein by reference.

The invention allows the interventional radiologist faster, easier and safer access to remote endovascular destinations. The contrast agent used in magnetic resonance angiography is much safer than iodinated contrast used in x-ray angiography. Exposure to x-rays is also eliminated. In addition, much less manipulation of the catheter is required to reach the destination vessels, thereby reducing the possibility of complications such as bleeding at the puncture site, and picking off plaques or causing dissections in the vessels en route. The advantages may be attributed, at least in part to the following: the catheter does not have to be as stiff since internal torque is not required to steer the tip of the catheter; sharp angulation of the catheter tip can be accomplished readily; gadolinium diethylene triamine pentaacetate (GdDTPA) is used for imaging rather than iodinated contrast material; guidewires are not required or are used less frequently; small vessels can be visualized even in the absence of contrast material; and no ionizing radiation is used.

In addition to the advantages for guiding the catheter to the target vessel, the MR therapy system allows monitoring of the application of heat or cold and will provide greater anatomic and functional information by virtue of the MR imaging technique.

The following examples are intended to provide those of ordinary skill in the art with a complete disclosure and description of how to make and use the novel devices of the invention, and are not intended to limit the scope of what the inventors regard as their invention in any way. Efforts have been made to insure accuracy with respect to numbers used (e.g., current amplitude, catheter diameters, etc.) but some experimental errors and deviations should be accounted for. Unless indicated otherwise, parts or parts by weight, molecular weight is weight average molecular weight; temperature is in degrees centigrade; current is in mA; magnetic field strength is in Tesla, and pressure is at or near atmospheric.

EXAMPLE 1

The use of a coil to impart motion to—or to provide orientation of—a catheter for interventional MRI requires adequate force to move or orient the tip of the catheter. This force must be generated by the interaction between the current in the coil and the ambient MR magnetic field. This study is based on the characteristics of three catheters presently in use. A deflection of 2.0 mm was set as the target for the calculation.

Three catheters were measured to determine dimensions and material characteristics. Meaningful tip deflections and the forces required for their production were estimated. Coils for other applications were investigated to evaluate fabrication feasibility. Deflections with a coil on one of the catheters was calculated in detail. An extrapolation was made to other catheters.

The analysis shows that deflections of 2.0 mm or larger can be produced easily in two of the catheters available. (The third catheter has a permanent deformation at the tip and, though measured, was not considered here.) A 60 turn solenoidal coil near the catheter tip was considered and found to be well within the range of coils used for other purposes. A conductor diameter of about 10% of that of the catheter was chosen for the study. The energized coil produces a maximum field on the order of 10 gauss, which will affect local MRI viewing, but only during steering current application. In alternating mode, it would not interfere with imaging. The heat generated by the coil is a small fraction of a milliwatt so heating will probably not be an issue even if the coil were on for a long period of time.

A. Catheter Shapes and Dimensions

Three catheters described in Table I were tested. The "French" sizes are based on the manufacturer's information supplied with the catheters. These catheters were measured to determine dimensions and the relation between "French" sizes and SI and English units. Results of the diameter measurements are listed in Table II. An approximate empirical relation between French sizes and SI outside diameter was found (I)

$$d_o(mm) = 0.28 + 0.1F + 0.045F^2. \quad (I)$$

TABLE I

CATHETER DESCRIPTIONS.

| CATHETER COMPANY | FRENCH SIZE # | LENGTH (mm) | DIAMETER (mm) | DIAMETER (in) |
|---|---|---|---|---|
| BALT | 3 | 1200 | 0.965 | 0.038 |
| | 2.5 | +250 | 0.787 | 0.031 |
| | 1.5 | +200 | 0.559 | 0.022 |
| TRACKER ® 10 | 2.6 | 1150 | 0.838 | 0.033 |
| | 2.0 | +150 | 0.686 | 0.027 |
| CORDIS SUPERTORQUE | 4.0 | 1100 | 1.397 | 0.055 |

TABLE II

CATHETER OUTSIDE DIAMETERS IN FRENCH, SI, AND ENGLISH UNITS

| FRENCH | mm | inches |
|---|---|---|
| 1.5 | 0.550 | 0.022 |
| 2 | 0.675 | 0.027 |
| 2.6 | 0.825 | 0.033 |
| 3 | 0.950 | 0.038 |
| 4 | 1.375 | 0.055 |

In addition to the overall dimensions of the catheters, the wall thickness of the BALT 1.5 French catheter was measured to be 0.0045" or 0.1125 mm. The Cordis Supertorque was permanently bent at the tip to allow easier entry into a vessel. As a result, the Cordis material was much stiffer than that used for the other two catheters. It is not considered appropriate for the type of deflections of interest in this study.

B. Catheter Material Elastic Modulus

The modulus of the smallest catheter section—BALT 1.5 French—was measured under simple tension. The catheter was supported over a circular rod so that the entire 200 mm tip section was hanging freely. Tape placed at the top end of this section provided a clear reference point about 20 cm from the tip (end) of the catheter. A very light compression clamp was attached near the tip and connected a nylon monofilament to the catheter. The nylon was fashioned to support weights of a few grams. The vertical distance from the bottom of the tape to the top of the compression clamp was used to determine catheter extension or strain. Table III shows the length of the catheter as a function of the applied weight.

TABLE III

EXTENSION OF THE 1.5 FRENCH CATHETER SECTION FOR VARIOUS APPLIED WEIGHTS

| WEIGHT (kg) | LENGTH (m) | EXTENSION (m) | Δl/l (ε) |
|---|---|---|---|
| 0 | 0.1922 | 0 | 0 |
| 0.0027 | 0.1970 | 0.0047 | 0.0247 |
| 0.0054 | 0.2016 | 0.0094 | 0.0489 |
| 0.0080 | 0.2059 | 0.0137 | 0.0713 |
| 0.0107 | 0.2100 | 0.0178 | 0.0926 |
| 0.0054 | 0.2035 | 0.0113 | 0.0585 |
| 0 | 0.1939 | 0.0017 | 0.0088 |

These extensions were used to determine the stress in the catheter and the modulus E of the catheter material. This required a measurement of the cross section of the catheter. Based on the measured wall thickness of 0.0045", and an outside diameter of 0.022" (0.55 mm), the catheter area is 0.000247 in² or 0.1596 mm². The modulus of the material is determined from the measured strain e due to the applied stress σ.

$$E = \frac{\sigma}{\varepsilon} = \frac{F}{A \cdot \varepsilon}. \quad (II)$$

The values found for the modulus for the catheter material at various extensions are given in Table IV. As the force is increased the modulus appears to increase slightly. The effect is probably associated with measurement accuracy and the large value of the strain. The maximum allowable strain for many materials is less than 0.003, as compared to the maximum measurement of 0.09 that was observed here. For the calculations below, the effective modulus of the catheter material is assumed to be 1000 psi (6.8 MPa), which is quite small. For comparison, the modulae of steel, aluminum, and structural wood are 30 million psi, 10 million psi, and 1.5 million psi.

TABLE IV

MODULUS OF ELASTICITY FOR THE FOUR DIFFERENT WEIGHTS AND EXTENSIONS GIVEN ABOVE

| STRESS (N) | MODULUS (MPa) | STRESS (psi) | MODULUS (psi) |
|---|---|---|---|
| 164548 | 6.66 | 24.265 | 981.8 |
| 329096 | 6.73 | 48.530 | 992.3 |
| 493644 | 6.93 | 72.795 | 1021.3 |
| 658193 | 7.11 | 97.060 | 1048.0 |

C. Catheter Deflections

Structures such as the tubular materials used for catheters can be deflected in a direction transverse to their longitudinal axis by both transverse forces and transverse torques. The magnitude of the deflection depends on the catheter shape, the materials used, the moment of inertia of the section and the length of the section being deformed. These deflections are given by the standard theory of elastic beams. (See for example William Riley and Loren Zachary, *Introduction to Mechanics of Material*, John Wiley and Sons, New York, 1989.) The deflection Y due to a force F at the end of a beam that is unsupported over a length L is:

$$Y = \frac{F}{6EI}(x^3 - 3Lx^2), \quad (III)$$

where E is Young's modulus for the material, I the moment of inertia of the structure, and x is the distance from the end of the constraint.

Similarly, a torque T applied to the free end of the catheter will produce a deflection:

$$Y = \frac{T}{2EI}x^2. \quad (IV)$$

The moment of inertia I of a beam has units length$^4$, and depends only on the geometry of the cross section. For example, a solid rod of radius r has a moment of inertia:

$$I = \pi \cdot r^4/4. \quad (V)$$

A hollow tube, such as a catheter, with inside and outside radii $r_i$ and $r_o$, has a moment of inertia given by:

$$I = \pi(r_o^4 - r_i^4)/4 \approx \pi(r_{av}^3 \Delta r). \quad (VI)$$

D. Effects on a Coil in a Magnetic Field

In this section we calculate the forces that can be produced by a coil in a magnetic field. The local dF on each section ds of a conductor carrying a current i in a magnetic field is perpendicular to both the direction of the current and direction of the applied magnetic field B:

$$df = i \cdot ds \otimes B. \quad (VII)$$

When the conductor is wound into a coil there are two types of effects on the coil. The first is an outward (or inward) force on the conductor. This force produces a hoop-type of load on the coil. If the external field is constant, then there is no net force on the coil that will tend to displace it. However, if there is a field gradient there will be a net force. It is this force associated with a magnetic gradient that is used in electric motors. The second force on a coil is a twisting force—or torque, which depends on the orientation of the coil with respect to the external field. This torque will cause an unconstrained coil to rotate to the orientation where the coils internal self field and the external field are parallel. The torque T produced by a rigid coil with a magnetic moment M in a field B is given by:

$$|T| = |M \otimes B| = MB \sin(\theta). \quad (VIII)$$

The moment of the coil is given by the product of the current, i, the number of turns, n, and the effective area.

$$M = \pi n i (r_o + r_w)^2 v. \quad (IX)$$

where v is a unit vector in the direction of the axis of the coil or, equivalently, the normal to the coil area, $r_o$ is the outer radius of the catheter, and $r_w$ is the radius of the wire. Here it is assumed that a solenoidal coil is wound around the outside of the catheter. Other coil geometries for the tip of a catheter are also possible. However, the torque can be obtained by the above equation once the magnitude of the magnetic moment is known either by calculation or measurement. Of course, the torque produced by the other coils will be in a direction different from that of the solenoid depending on coil orientation.

E. Coils and Coil Materials

Very small coils have been used for nuclear magnetic resonance studies. Typical coils that are used are 0.4 mm id, 3 to 4 mm long, and use a 0.05 mm diameter copper wire.

Several samples of copper wire were obtained from New England Electric Wire to evaluate their dimensions and to determine if the resistivity was similar to the quoted $1.8 \cdot 10^{-8}$ Ohm meters for copper at room temperature. Material sufficient for several test coils is available. The quoted resistance of the larger wires was correct to the accuracy of the dimensional measurements, ±0.0003 in. Table V shows the measured dimensions of the wires tested.

TABLE V

Measured dimensions of small diameter copper wires

| Wire | Meas. Diam. (in) | Meas. Diam. (mm) | Meas. Resistance (Ohms/m) | Nom. Diameter (in) | Nom. Resistance Ohms/1000 ft. |
|---|---|---|---|---|---|
| 36 | 0.0053 | 0.1346 | 1.3 | 0.0050 | 415 |
| 38 | 0.0044 | 0.1118 | 2 | 0.0040 | 648 |
| 40 | 0.0032 | 0.0813 | 3.2 | 0.0031 | 1079 |
| 42 | 0.0029 | 0.0737 | 5 | 0.0026 | 1659 |
| 44 | 0.0024 | 0.0610 | 8 | 0.0020 | 2593 |
| 46 | 0.0019 | 0.0483 | 13 | 0.00157 | 4207 |
| 50 | 0.0013 | 0.0330 | 30 | 0.00099 | 10580 |

F. Deflections in a Catheter

The torque required to cause a deflection in the 1.5 French BALT catheter will be calculated below using the relations developed in the previous sections. The first issue is to determine the required magnitude for the deflection. For this estimate we assume that: (1) the catheter is inside a vessel and must be deformed at the tip to enter a smaller vessel; (2) a tip deflection of 2.0 mm is sufficient to allow catheter redirection into the smaller vessel; (3) the catheter is unconstrained over a length of 20 mm; and (4) a coil with 60 turns of 40 Gauge wire is wound on the outside of the catheter.

The moment of inertia of the BALT, 1.5 French, catheter is:

$$I = \pi(r_o^4 - r_i^4)/4 = \pi(0.275^4 - 0.165^4)/4 = 0.00391 \text{ mm}^4. \quad (XI)$$

Using this moment of inertia and the measured modulus E it is possible to calculate the torque required to produce the 2.0 mm deflection:

$$T = 2\frac{YEI}{L^2} = 2 \cdot 0.002 \cdot 6.8 \cdot 10^6 \cdot 3.91 \cdot 10^{-15} \quad (XII)$$

$$= 2.65 \cdot 10^{-7} \text{ newton} \cdot \text{meters}$$

The magnetic moment required to produce a torque of this magnitude in a field of 1.5 T is:

$$M = T/B = 2.65 \cdot 10^{-7}/1.5 = 1.77 \cdot 10^{-7} (A \cdot m^2), \quad (XIII)$$

where we have assumed that $\sin(\theta) = 1$. From this value it is possible to calculate the current required in the 60 turn coil:

$$i = \frac{M}{\pi \cdot n \cdot (r_o + r_w)^2} \quad (XIV)$$

$$= \frac{1.77 \cdot 10^{-7}}{\pi \cdot n \cdot (0.27 + 0.0407)^2 \cdot 10^{-6}} = 0.0094 \text{ A}.$$

This coil will produce a peak magnetic field of about 10 gauss (1 mT) which will certainly affect MRI operation. Thus the coil must be energized for short periods between observations of its position.

G. Heating Effects in the Coil

The electrical current produces Joule heating which will raise the temperature of the coil. To calculate this effect we use the resistance for 40 Gauge wire and the specific heat of copper, $C_v=4.1 J/cc/°C$. The temperature rise is:

$$\frac{dT}{dt} = \frac{i^2}{C_v \cdot V} = \frac{0.0094^2 \cdot 3.2}{4.1 \cdot 0.00519} = 0.0133 \frac{°C}{second}. \quad (XV)$$

The power generated in the coil is 0.053 mW, which implies that a continuous current can probably be allowed in the coil as very little heat is generated. Larger forces and larger deflections should be possible and electronics for short duration pulses should be fairly simple to create.

H. Motion in Catheters of Other Sizes—Scale-up

The calculations to this point have been based on the smallest catheter available, the BALT 1.5 French. It will be useful to estimate the scaling to a larger size catheter. If we assume that the conductor diameter increases as the catheter diameter increases, then the deflection becomes $$Y = \frac{M}{2EI} L^2 \quad (XVI)$$
$$= \frac{4\pi \cdot n \cdot i(r_o + + r_w)^2 BL^2}{2E\pi(r_0^4 - r_i^4)}$$
$$= \frac{2\pi n j r_w^2 (r_0 + r_w)^2 BL^2}{E(r_0^4 - r_i^4)} \propto \frac{njBL^2}{E},$$

where the current density, $$j = i/\pi \cdot r_w^2, \quad (XVII)$$

has been used because the local heating (dT/dt) in two conductors of different diameter will be the same if the current density is the same. Since B and E are the same for the two cases, the different deflection will depend only on the unsupported length, L, and the number of turns in the coil. The following can be said about scale up based on the above approach: (1) the current required will increase as the square of the diameter of the catheter, $d^2$; (2) the total power input (W) will increase as the volume of conductor, i.e., $d^3$; (3) catheters up to at least French 4 can be deflected so long as the modulus does not change; (4) the field produced by the coil will be proportional to the catheter diameter; and (5) deflection of catheters is proportional to B and j, therefore operation at 0.5 T should be possible.

EXAMPLE 2

A 25–30 turn solenoidal coil was wound on a 1.2 mm former, using 36-gauge insulated copper wire. The coil was inserted in a tube containing 0.9% (standard physiological) saline. Imaging was performed using a 2 T Omega CSI-II system (Bruker Instruments, Fremont, Calif.) and a 55 mm i.d. birdcage transmit/receive RF coil. Four experimental paradigms were applied: (1) phantom (saline in test tube only, no micro-coil); (2) phantom with inactive (no current) micro coil inserted, oblique to main field axis; (3) as in (2), with 10 mA current flowing in coil, (4) as in (2) with no current flowing, immediately after current shut-off. A gradient-recalled-echo imaging sequence was used with the following parameters: TR/TE/flip: 100ms/3ms/30°. Two signal averages were acquired, thus a total imaging time (128 matrix) of 25 seconds was required.

Homogenous signal intensity across the saline phantom was observed. The coil was clearly visualized as a signal void against the homogeneous background. Slight blurring could be seen, but no significant susceptibility artifact was observed (FIG. 6). Significant signal voiding extending well beyond the coil was observed due to the current in the coil (FIG. 7). No residual artifact was observed. The image obtained immediately post-current was identical to that prior to current application (subtraction yielded pure noise) (FIG. 8). No motion was detected from the application of current, due primarily to mechanical resistance of the coil in contact with the tube walls. In the absence of the test tube, clear motion of the coil was observed, when current was applied to the coil, oriented within the 2T magnet, oblique to the main field axis. Thus the coil can be visualize using typical MRI sequences without significant susceptibility artifact. During steering, the current rendered coil visualization impractical; however, no residual effects were seen after current shutoff. As the coil easily became visible, switching between visualization and movement of the coil is feasible. The coil was noted to align with the magnetic field when a current is applied, generating a magnetic moment. In general (in the absence of external restraint) motion did occur and was optically visible.

EXAMPLE 3
Coil Testing: Dynamic Imaging of Coil Deflection

The objectives of this study are to deflect a solenoidal coil carrying current in the magnetic field of an MRI system and to image dynamically a the coil by the passage of electric current within its turns.

A 25–30 turn solenoidal coil of 36-gauge drawn copper wire was used. The coil was suspended vertically in a vessel containing approximately 100 ml distilled water containing few drops of GdDTPA to improve MRI visualization. The coil was suspended approximately 3.5 cm from its fixed point and was completely immersed in the water. Imaging was performed using a 2 T Omega CSI-II system (Bruker Instruments, Fremont, Calif.). In addition to high resolution spin echo positioning images, dynamic single slice gradient-recalled echo images were acquired in a sagittal plane containing the coil and with a slice thickness of 2 mm (spoiled gradient recalled acquisition (SPGR) pulse sequence TR=12 ms, TE=2.4 ms, flip-angle about 60°). Image acquisition time (128×128 matrix, 50 mm field of view) was approximately 1 second. Sets of 16 dynamic images were acquired with alternating period of no current, +ve current, no current, –ve current and no current, each period lasting 2—3 image acquisitions. In three permutations of this experiment, current levels of ±38 mA (FIG. 9A), ±58 mA (FIG. 9B) and ±130 mA (FIG. 9C) were used. The indicated current was applied for a period of approximately two to three seconds and held constant during that period. The peak-to-peak deflection of the coil tip was measured for each current level. "Peak-to-peak" is used to indicate the displacement of the coil tip between positively applied current and negatively applied current.

FIGS. 9A, 9B and 9C each shows 16 images acquired with the above protocol. In each case, the resting coil can be visualized as a thin signal void. Under application of current, a magnetic field disturbance can be seen (as extended signal voiding). Nevertheless, deflection can be resolved. The magnitude of both current-induced signal voiding and deflection appears to increase with increasing current. The sense of the deflection corresponds to the polarity of the applied current.

Figures 10A, 10B:
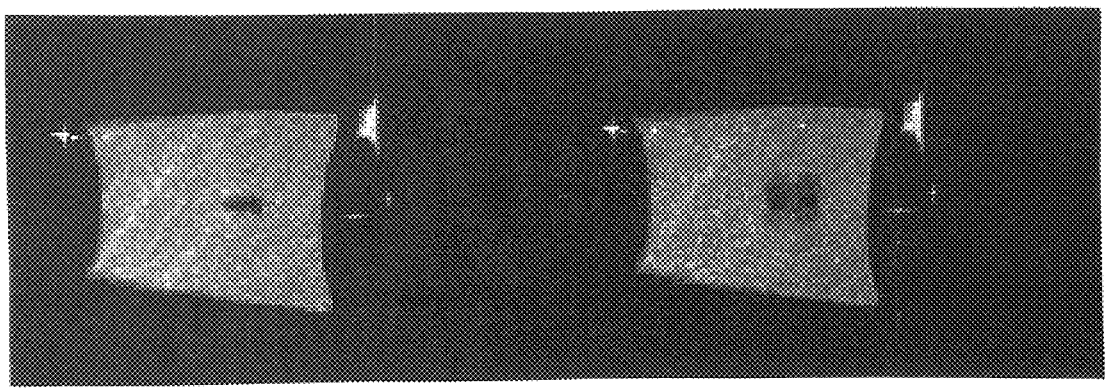
FIGS. 10A, 10B, 10C and 10D are overlaid images corresponding to positive and negative coil deflections in response to 0 mA, 38 mA, 58 mA and 130 mA, respectively.
Figures 10C, 10D:
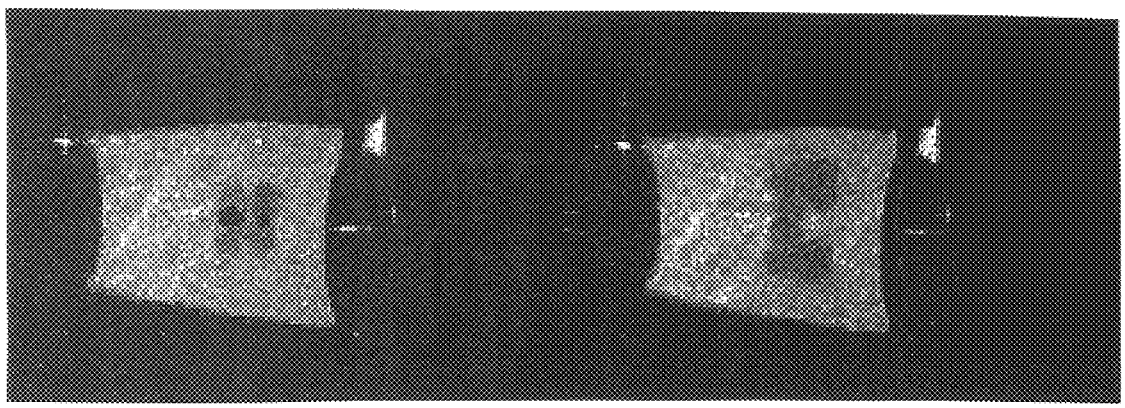

By taking overlaid images (see, FIG. 10) corresponding to the maximum positive and negative deflections under the four current conditions (0 mA (FIG. 10A), 38 mA (FIG. 10B), 58 mA (FIG. 10C) and 130 mA (FIG. 10D)), it is possible to measure the "peak-to-peak" deflection. FIG. 11 shows a plot of the end tip "peak-to-peak" deflection, measured from the images in FIG. 9, as a function of applied current.

These results indicate that applying current to a solenoidal coil suspended perpendicular to a 2T magnetic field can cause a deflection toward the field axis. The deflection can be imaged dynamically using high-speed MRI. The sense of the deflection corresponds to the polarity of the applied current. The magnitude of the deflection scales approximately linearly with applied current. The signal-voiding artifact caused by electric current flowing in the coil increases with applied current, but does not obscure visualization of the deflection.

While the present invention has been described with respect to specific embodiments, many modifications, variations, alterations, substitutions, and equivalents will be apparent to those skilled in the art.

We claim:

1. An apparatus for orienting a directable device, comprising;
   (a) a directable device adapted for insertion into a patient comprising a substrate wrapped with a multi-coil package comprising overlapping or overlaid coaxial coils, which package is adapted for conducting multiple, independent electric currents such that when the currents are passed through the multi-coil package a local directable magnetic moment is created;
   (b) a means for selectively applying electric currents through the multi-coil package to orient the substrate; and
   (c) a means external to the patient for generating a magnetic field to which the directable device is exposed,
   wherein the local directable magnetic moment is at a controllable angle with respect to the substrate to orient the substrate in the magnetic field.

2. The apparatus of claim 1, wherein the means for generating an external magnetic field is generated by a magnet of a magnetic resonance imaging device.

3. The apparatus of claim 1, wherein the directable device further comprises a transmit/receive coil.

4. The apparatus of claim 3, wherein the transmit/receive coil is one or more coils in the multi-coil package.

5. The apparatus of claim 1, wherein the directable device further comprises a receiver coil.

6. The apparatus of claim 5, wherein the receiver coil is one or more coils in the multi-coil package.

7. The apparatus of claim 1, wherein the multi-coil package comprises three coils, wherein each coil is capable of independently conducting electric current such that currents passed through the individual coils produce three mutually orthogonal magnetic moments.

8. The apparatus of claim 7, wherein the directable device further comprises a transmit/receive coil.

9. The apparatus of claim 8, wherein the transmit/receive coil is a coil of the multi-coil package.

10. The apparatus of claim 7, wherein the directable device further comprises a receiver coil.

11. The apparatus of claim 10, wherein the receiver coil is a coil of the multi-coil package.

12. The apparatus of claim 7, wherein the directable device is a catheter comprising an elongate tube having a proximal end; a distal end comprising a tip; an inner surface; an outer surface; and a wall interposed between the inner and outer surfaces.

13. The apparatus of claim 12, wherein the three coils are situated near the tip of the distal end of the elongate tube.

14. The apparatus of claim 12, wherein the three coils of the multi-coil package are situated on the outer surface of the elongate tube.

15. The apparatus of claim 12, wherein the three coils are embedded in the wall of the elongate tube.

16. The apparatus of claim 12, wherein the catheter further comprises a sheath that encases the multi-coil package.

17. The apparatus of claim 12, wherein the means for applying electric currents through the coils comprises electric leads attached to each of the coils and to sources of electric current.

18. The apparatus of claim 12, wherein the means for applying electric currents through the coils comprises a source of a radio frequency (RF) energy.

19. The apparatus of claim 12, wherein the catheter further comprises at least one of a means for performing an interventional diagnostic action or a means for performing an interventional therapeutic activity.

20. The apparatus of claim 19, wherein the means for performing an interventional diagnostic action is selected from the group consisting of means for introducing a radiographic diagnostic agent, means for taking a biopsy sample, means for local delivery of electric current, means for performing cryosurgery, means for performing hyperthermia treatments, means for introducing a stent, means for introducing a balloon placement, means for administering a pharmacologic agent, means for performing electrocautery, means for deploying a coil, and means for deposing a radioactive implant.

21. The apparatus for claim 1, wherein the directable device is a catheter comprising an elongate tube having a proximal end; a distal end, which distal end is intended to be situated in a body cavity, duct or vessel and comprises tip; an inner surface; an outer surface; and a wall interposed between the inner and outer surfaces.

22. The apparatus for claim 21, wherein the multi-coil package is situated near the tip of the distal end of the elongate tube.

23. The apparatus of claim 21, wherein the multi-coil package is situated on the outer surface of the elongate tube.

24. The apparatus of claim 21, wherein the multi-coil package is embedded in the wall of the elongate tube.

25. The apparatus of claim 21, wherein the catheter further comprises a sheath that encases the multi-coil package.

26. The apparatus of claim 21, wherein the means for applying electric currents through the multi-coil package comprises electric leads attached to the multi-coil package and to sources of electric current.

27. The apparatus of claim 21, wherein the means for applying electric currents through the multi-coil package comprises a source of a radio frequency (RF) energy.

28. The apparatus of claim 21, wherein the catheter further comprises at least one of a means for performing an interventional diagnostic action or a means for performing an interventional therapeutic activity.

29. The apparatus of claim 28, wherein the means for performing an interventional diagnostic action is selected from the group consisting of means for introducing a radiographic diagnostic agent, means for taking a biopsy sample, means for local delivery of electric current, means for performing cryosurgery, means for performing hyperthermia treatments, means for introducing a stent, means for introducing a balloon placement, means for administering a pharmacologic agent, means for performing electrocautery, means for deploying a coil, and means for depositing a radioactive implant.

30. The apparatus of claim 1, wherein the device is a guide wire.

31. The apparatus of claim 1, wherein the means for applying electric currents through the multi-coil package comprises electric leads attached to each coil of the multi-coil package and to sources of electric current.

32. The apparatus of claim 1, wherein the means for applying an electric current through the multi-coil package comprises a source of a radio frequency (RF) energy.

33. The apparatus of claim 32, 27, or 18, wherein the source of RF energy is a RF transmit coil of a magnetic resonance imaging apparatus.

34. The apparatus of claim 1, wherein the multi-coil package comprises three coil layers.

35. The apparatus of claim 1, wherein the multi-coil package comprises concentric layers.

36. The apparatus of claim 1, wherein the multi-coil package comprises concentric coils.

37. A method of orienting a directable device, comprising:
   (a) inserting a directable device into a patient, the directable device comprising a substrate wrapped with a multi-coil package comprising overlapping or overlaid coaxial coils, which package is adapted for conducting electric currents such that currents passed through the multi-coil package create a local directable magnetic moment;
   (b) selectively applying independent electric currents through individual coils of the multi-coil package to orient the substrate; and
   (c) generating a magnetic field external to the patient at a strength and frequency sufficient to effect orienting of the directable device in a desired direction;
   wherein the local directable magnetic moment is at a controllable angle with respect to the substrate to orient the substrate in the external magnetic field.

38. The method of claim 37, wherein the means for generating an external magnetic field is a magnet of a magnetic resonance imaging device.

39. The method of claim 37, wherein the directable device further comprises a transmit/receive coil.

40. The method of claim 39, wherein the transmit/receive coil is one or more coils in the multi-coil package.

41. The method of claim 37, wherein the directable device further comprises a receiver coil.

42. The method of claim 41, wherein the receiver coil is one or more coils in the multi-coil package.

43. The method of claim 37, wherein the multi-coil package comprises three coils, wherein each coil is capable of independently conducting electric current such that currents passed through the coils produce three mutually orthogonal magnetic moments.

44. The method of claim 43, wherein the directable device further comprises a transmit/receive coil.

45. The method of claim 44, wherein the transmit/receive coil is one or more coils of the multi-coil package.

46. The method of claim 43, wherein the directable device further comprises a receiver coil.

47. The method of claim 46, wherein the receiver coil is one or more coils of the multi-coil package.

48. The method of claim 43, wherein the directable device is a catheter comprising an elongate tube having a proximal end, a distal end comprising a tip, an inner surface, an outer surface, and a wall interposed between the inner and outer surfaces.

49. The method of claim 48, wherein the three coils are situated near the tip of the distal end of the elongate tube.

50. The method of claim 48, wherein the three coils are situated on the outer surface of the elongate tube.

51. The method of claim 48, wherein the three coils are embedded in the wall of the elongate tube.

52. The method of claim 48, wherein the catheter further comprises a sheath that encases the multi-coil package.

53. The method of claim 48, wherein the means for applying electric currents through the coils comprises electric leads attached to each of the coils and to sources of electric current.

54. The method of claim 48, wherein the means for applying electric currents through the coils comprises a source of a radio frequency (RF) energy.

55. The method of claim 48, wherein the catheter further comprises at least one of a means for performing an interventional diagnostic action or a means for performing an interventional therapeutic activity.

56. The method of claim 55, wherein the means for performing an interventional diagnostic action is selected from the group consisting of means for introducing a radiographic diagnostic agent, means for taking a biopsy sample, means for local delivery of electric current, means for performing cryosurgery, means for performing hyperthermia treatments, means for introducing a stent, means for introducing a balloon placement, means for administering a pharmacologic agent, means for performing electrocautery, means for deploying a coil, and means for depositing a radioactive implant.

57. The method of claim 37, wherein the directable device is a catheter comprising an elongate tube having a proximal end, a distal end comprising a tip, an inner surface, an outer surface, and a wall interposed between the inner and outer surfaces.

58. The method of claim 57, wherein the multi-coil package is situated near the tip of the distal end of the elongate tube.

59. The method of claim 57, wherein the multi-coil package is situated on the outer surface of the elongate tube.

60. The method of claim 57, wherein the multi-coil package is embedded in the wall of the elongate tube.

61. The method of claim 57, wherein the catheter further comprises a sheath that encases the multi-coil package.

62. The method of claim 57, wherein the means for applying electric currents through the multi-coil package comprises electric leads attached to individual coils of the multi-coil package and to sources of electric current.

63. The method of claim 57, wherein the means for applying electric currents through the coils comprises a source of a radio frequency (RF) energy.

64. The method of claim 57, wherein the catheter further comprises at least one of a means for performing an interventional diagnostic action or a means for performing an interventional therapeutic activity.

65. The method of claim 64, wherein the means for performing an interventional diagnostic action is selected from the group consisting of means for introducing a radiographic diagnostic agent, means for taking a biopsy sample, means for local delivery of electric current, means for performing cryosurgery, means for performing hyperthermia treatments, means for introducing a stent, means for introducing a balloon placement, means for administering a pharmacologic agent, means for performing electrocautery, means for deploying a coil, and means for depositing a radioactive implant.

66. The method of claim 37, wherein the device is a guide wire.

67. The method of claim 37, wherein the means for applying electric currents through the multi-coil package comprises electric leads attached to the multi-coil package and to sources of electric current.

68. The method of claim 37, wherein the means for applying electric currents through the coils comprises a source of a radio frequency (RF) energy.

69. The method of claim 59, 63, or 54, wherein the source of RF energy is a RF transmit coil of a magnetic resonance imaging apparatus.

70. The method of claim 37, wherein the multi-coil package comprises three coil layers.

71. The method of claim 37, wherein the multi-coil package comprises concentric layers.

72. The method of claim 37, wherein the multi-coil package comprises concentric coils.

73. A directable catheter comprising:
(a) a flexible elongate substrate having a proximal end and a distal end adapted to be situated in a body cavity, duct or vessel, wherein the distal end comprises a tip; and
(b) a multi-coil package comprising overlapping or overlaid coaxial coils, which multi-coil package is attached to the substrate, the multi-coil package comprising a conductive material, wherein the multi-coil package is adapted for conducting multiple, independent electric currents such that currents passed through the multi-coil package create a local directable magnetic moment;
wherein the local directable magnetic moment is at a controllable angle with respect to the substrate to provide a torque to orient the substrate in a magnetic field generated external to the body cavity, duct or vessel.

74. The directable catheter of claim 73, wherein the multi-coil package comprises three coils, each coil being capable of independently conducting electric current such that current passed through the coils produces three mutually orthogonal magnetic moments.

75. The directable catheter of claim 74, wherein the multi-coil package is embedded in the substrate.

76. The directable catheter of claim 74, wherein the multi-coil package is wrapped around an outer surface of the substrate.

77. The directable catheter of claim 74, further comprising a transmit/receive coil.

78. The directable catheter of claim 77, wherein the transmit/receive coil is one of the three coils.

79. The directable catheter of claim 74, further comprising a receiver coil.

80. The directable catheter of claim 79, wherein the receiver coil is one of the coils of the multi-coil package.

81. The directable catheter of claim 74, wherein the multi-coil package is situated near the tip of the distal end of the elongate substrate.

82. The directable catheter of claim 74, wherein the catheter further comprises a sheath encasing the multi-coil package.

83. The directable catheter of claim 73, wherein the multi-coil package is embedded in the substrate.

84. The directable catheter of claim 73, wherein the multi-coil package is wrapped around an outer surface of the substrate.

85. The directable catheter of claim 73, further comprising a transmit/receive coil.

86. The directable catheter of claim 85, wherein the transmit/receive coil is one or more coils of the multi-coil package.

87. The directable catheter of claim 86, wherein the receiver coil is one or more coils of the multi-coil package.

88. The directable catheter of claim 73, further comprising a receiver coil.

89. The directable catheter of claim 73, wherein the multi-coil package is situated near the tip of the distal end of the elongate substrate.

90. The directable catheter of claim 73, wherein the catheter further comprises a sheath encasing the multi-coil package.

91. The directable catheter of claim 73, wherein the multi-coil package comprises three coil layers.

92. The directable catheter of claim 73, wherein the multi-coil package comprises concentric layers.

93. The directable catheter of claim 73, wherein the multi-coil package comprises concentric coils.

94. The directable catheter of claim 73, wherein the substrate is tubular.

95. The directable catheter of claim 73, wherein the substrate comprises an inner wall and an outer wall.

* * * * *